United States Patent [19]

Möller et al.

[11] Patent Number: 4,503,244

[45] Date of Patent: Mar. 5, 1985

[54] SEBOSUPPRESSIVE TOPICAL COSMETIC PREPARATIONS CONTAINING ALKOXYBENZOIC ACID ESTERS, PROCESS FOR INHIBITING SEBUM PRODUCTION AND ALKOXYBENZOIC ACID ESTERS

[75] Inventors: Hinrich Möller; Siegfried Wallat, both of Monheim, Fed. Rep. of Germany

[73] Assignee: Henkel Kommanditgesellschaft, Duesseldorf, Fed. Rep. of Germany

[21] Appl. No.: 560,582

[22] Filed: Dec. 12, 1983

[30] Foreign Application Priority Data

Jan. 17, 1983 [DE] Fed. Rep. of Germany ....... 3301313

[51] Int. Cl.³ .............................................. C07C 69/76
[52] U.S. Cl. ..................... 514/544; 560/74; 560/64
[58] Field of Search ................. 560/64, 74; 424/308, 424/309

[56] References Cited

U.S. PATENT DOCUMENTS 2,176,070 10/1939 Grether et al. ................ 560/64
4,138,579 2/1979 Chodnekar et al. ............ 560/64

FOREIGN PATENT DOCUMENTS 883234 11/1961 United Kingdom ............ 560/64
888681 1/1962 United Kingdom ............ 560/64

Primary Examiner—Paul J. Killos
Attorney, Agent, or Firm—Ernest G. Szoke; Nelson Littell, Jr.; Henry E. Millson, Jr.

[57] ABSTRACT

A topical cosmetic preparation for the treatment of seborrhea containing a sebosuppressively effective amount of at least one alkoxybenzoic acid ester having the formula

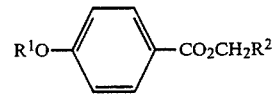

wherein $R^1$ represents a $C_{6-20}$-n-alkyl and $R^2$ is a member selected from the group consisting of $-CH_2OR^3$, $-C_2H_4OR^3$, $-CH_2OC_2H_4OR^3$, $-CH_2OH$, $-C_2H_4OH$, $-CH(CH_3)OH$, $-CH_2NR^3R^4$, $-C_2H_4NR^3R^4$, $-CO_2R^3$ and $-CH_2CO_2R^3$, wherein $R^3$ and $R^4$ are $C_{1-4}$-alkyl, as an antiseborrheic, and further containing conventional vehicles and additives for topical application; as well as the process for reducing sebaceous cell sebum production in a mammal in need thereof using the above cosmetic preparation; and the alkoxybenzoic acid esters of the above formula.

12 Claims, No Drawings

SEBOSUPPRESSIVE TOPICAL COSMETIC PREPARATIONS CONTAINING ALKOXYBENZOIC ACID ESTERS, PROCESS FOR INHIBITING SEBUM PRODUCTION AND ALKOXYBENZOIC ACID ESTERS

BACKGROUND OF THE INVENTION

This invention relates to topical cosmetic preparations containing certain alkoxybenzoic acid esters for improving the greasy and unaesthetic appearance of the hair and skin and to new alkoxybenzoic acid esters.

In modern cosmetology, efforts are constantly being made to reduce the greasy, unaesthetic appearance of the hair caused by excessive secretion of the sebaceous glands and of the scalp. Accordingly, frequent attempts have been made to normalize the secretion of the sebaceous glands by suitable preparations in order to restore the hair to its healthy appearance. Cosmetic preparations containing additions of sulfur, mercury or tar have been used to control seborrhea of the scalp. Unfortunately, it has been found that these known antiseborrheic additives frequently produce side effects in the event of prolonged use without giving really satisfactory results in regard to efficacy and performance properties.

German published application DE-OS No. 19 06 665 suggested N,N-diethyl-m-toluamide as an active substance for the treatment of dandruff caused by seborrhea. U.S. Pat. No. 3,755,604 suggests phenylpentadienoic acids to control the production of sebum. But it was found that neither N,N-diethyl-m-toluamide nor phenylpentadienoic acid show, however, fully satisfactory sebosuppressive properties. German published application DE-OS No. 29 26 267 describes 3,7,11-trimethyl-2,6,10-dodecatrien-1-ol derivatives as additives to cosmetic preparations for normalizing the secretion of sebum. Unfortunately, it has been found that these compounds also have only a very weak antiseborrheic effect.

OBJECTS OF THE INVENTION

An object of the present invention is to provide a cosmetic preparation which has a stronger effect than corresponding known preparations without any adverse consequences on the human body.

Another object of the present invention is the development of a topical cosmetic preparation for the treatment of seborrhea containing a sebosuppressively effective amount of at least one alkoxybenzoic acid ester having the formula

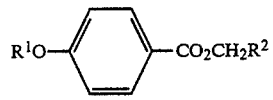

wherein $R^1$ represents a $C_{6-20}$-n-alkyl and $R^2$ is a member selected from the group consisting of $-CH_2OR^3$, $-C_2H_4OR^3$, $-CH_2OC_2H_4OR^3$, $-CH_2OH$, $-C_2H_4OH$, $-CH(CH_3)OH$, $-CH_2NR^3R^4$, $-C_2H_4NR^3R^4$, $-CO_2R^3$ and $-CH_2CO_2R^3$, wherein $R^3$ and $R^4$ are $C_{1-4}$-alkyl, as an antiseborrheic, and further containing conventional vehicles and additives for topical application.

A further object of the present invention is the development of a process for reducing sebaceous cell sebum production in a mammal in need thereof which comprises contacting said sebaceous cell in the skin of said mammal with an effective amount to reduce sebum production of at least one alkoxybenzoic acid ester having the formula

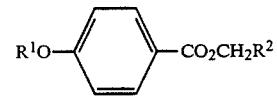

wherein $R^1$ represents a $C_{6-20}$-n-alkyl and $R^2$ is a member selected from the group consisting of $-CH_2OR^3$, $-C_2H_4OR^3$, $-CH_2OC_2H_4OR^3$, $-CH_2OH$, $-C_2H_4OH$, $-CH(CH_3)OH$, $-CH_{NR}{}^3R^4$, $-C_2H_4NR^3R^4$, $-CO_2R^3$ and $-CH_2CO_2R^3$, wherein $R^3$ and $R^4$ are $C_{1-4}$-alkyl.

A yet further object of the present invention is the obtaining of an alkoxybenzoic acid ester having the formula

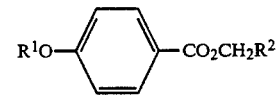

wherein $R^1$ represents a $C_{6-20}$-n-alkyl and $R^2$ is a member selected from the group consisting of $-CH_2OR^3$, $-C_2H_4OR^3$, $-CH_2OC_2H_4OR^3$, $-CH_2OH$, $-C_2H_4OH$, $-CH(CH_3)OH$, $-CH_2NR^3R^4$, $-C_2H_4NR^3R^4$, $-CO_2R^3$ and $-CH_2CO_2R^3$, wherein $R^3$ and $R^4$ are $C_{1-4}$-alkyl.

These and other objects of the invention will become more apparent as the description thereof proceeds.

DESCRIPTION OF THE INVENTION

It has now surprisingly been found that certain alkoxybenzoic acid esters show outstanding antiseborrheic effects, even in very small does.

Accordingly, the present invention relates to sebosuppressive cosmetic preparations which are characterized by a content of p-alkoxybenzoic acid esters corresponding to the following general formula I

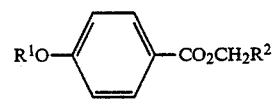

in which $R^1$ represents an n-alkyl radical containing from 6 to 20 carbon atoms, $R^2$ represents one of the groups $-CH_2OR^3$, $-C_2H_4OR^3$, $-CH_2OC_2H_4OR^3$, $-CH_2OH$, $-C_2H_4OH$, $-CH(CH_3)OH$, $-CH_2NR^3R^4$, $-C_2H_4NR^3R^4$, $-CO_2R^3$ or $-CH_2CO_2R^3$, where $R^3$ and $R^4$ may be the same or different and represent alkyl radicals containing from 1 to 4 carbon atoms.

More particularly, the present invention relates to a topical cosmetic preparation for the treatment of seborrhea containing a sebosuppressively effective amount of at least one alkoxybenzoic acid ester having the formula

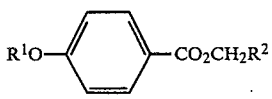

wherein $R^1$ represents a $C_{6\text{-}20}$-n-alkyl and $R^2$ is a member selected from the group consisting of —$CH_2OR^3$, —$C_2H_4OR^3$, —$CH_2OC_2H_4OR^3$, —$CH_2OH$, —$C_2H_4OH$, —$CH(CH_3)OH$, —$CH_2NR^3R^4$, —$C_2H_4NR^3R^4$, —$CO_2R^3$ and —$CH_2CO_2R^3$, wherein $R^3$ and $R^4$ are $C_{1\text{-}4}$-alkyl, as an antiseborrheic, and further containing conventional vehicles and additives for topical application; as well as to a process for reducing sebaceous cell sebum production in a mammal in need thereof which comprises contacting said sebaceous cell in the skin of said mammal with an effective amount to reduce sebum production of at least one alkoxybenzoic acid ester having the formula

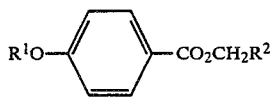

wherein $R^1$ represents a $C_{6\text{-}20}$-n-alkyl and $R^2$ is a member selected from the group consisting of —$CH_2OR^3$, —$C_2H_4OR^3$, —$CH_2OC_2H_4OR^3$, —$CH_2OH$, —$C_2H_4OH$, —$CH(CH_3)OH$, —$CH_2NR^3R^4$, —$C_2H_4NR^3R^4$, —$CO_2R^3$ and —$CH_2CO_2R^3$, wherein $R^3$ and $R^4$ are $C_{1\text{-}4}$-alkyl; and also to an alkoxybenzoic acid ester having the formula

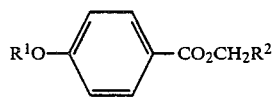

wherein $R^1$ represents a $C_{6\text{-}20}$-n-alkyl and $R^2$ is a member selected from the group consisting of —$CH_2OR^3$, —$C_2H_4OR^3$, —$CH_2OC_2H_4OR^3$, —$CH_2OH$, —$C_2H_4OH$, —$CH(CH_3)OH$, —$CH_2NR^3R^4$, —$C_2H_4NR^3R^4$, —$CO_2R^3$ and —$CH_2CO_2R^3$, wherein $R^3$ and $R^4$ are $C_{1\text{-}4}$-alkyl.

The compounds used in accordance with the invention are new. They may be produced by generally known methods.

For example, the alkoxyalkyl or hydroxyalkyl or other esters may be obtained from the corresponding p-alkoxy benzoic acid methyl esters by transesterification with suitable alcohol components containing radicals corresponding to $R^2$ above in the presence of alkaline catalysts, such as sodium methoxylate. The methanol liberated is removed from the equilibrium by distillation.

The p-alkoxy benzoic acid methyl esters are produced, for example, by alkylating p-hydroxy benzoic acid methyl ester with alkyl halides, sulfates or sulfonates containing alkyl radicals corresponding to $R^1$.

Conversely, it is also possible initially to esterify the p-hydroxy benzoic acid and then to carry out the alkylation step.

Another method of producing the new esters is to alkylate the alkali metal salts, particularly sodium salts, of p-alkoxy benzoic acids with alkyl halides, sulfates or sulfonates containing radicals corresponding to $R^2$ above. This method is particularly suitable for producing the p-alkoxy benzoic acid alkoxy carbonyl alkyl esters, the alkylating agents used being the corresponding halogen alkanoic acid esters.

Finally, it is also possible to use the direct esterification process in which the esters are formed from the corresponding p-alkoxy benzoic acids and alkanols containing radicals corresponding to $R^2$ above by dehydration in the presence of acid catalysts. Where a large excess of alcohol is used, the water of reaction may remain in the reaction mixture, otherwise it is removed from the equilibrium by suitable measures, for example distillation.

The claimed esters may be based, for example, on the following p-alkoxy benzoic acids: 4-hexyloxy-, 4-octyloxy-, 4-decyloxy-, 4-undecyloxy-, 4-dodecyloxy-, 4-tetradecyloxy-, 4-hexadecyloxy-, 4-octoadecyloxy- and 4-eicosyloxybenzoic acid.

The alcohol component may contain, for example, the following radicals (corresponding to $R^2$): 2-hydroxy ethyl, 2-hydroxypropyl, 3-hydroxypropyl, 2-methoxy ethyl, 2-ethoxy ethyl, 3-methoxy propyl, 2-diethylaminoethyl, 3-dimethylaminopropyl, methoxy-carbonylmethyl, ethoxycarbonylmethyl, propoxy-carbonylmethyl, and 2-methoxycarbonylethyl.

The compounds according to the invention show pronounced sebosuppressive activity combined with excellent compatibility with the skin and mucous membrane. They may be incorporated without difficulty in various cosmetic preparations, such as aqueous or alcoholic solutions, oils, suspensions, gels, emulsions, salves or aerosols. For treating seborrheic skin and greasy hair, these preparations may be applied in any of the usual forms, such as hair lotions, shampoos, hair treatments, hair rinses, skin lotions or shaking mixtures.

The cosmetic preparations according to the invention represent solutions of the effective compounds of formula I in water, in alcohol especially ethanol, in aqueous-alcoholic mixtures, in oil, as well as in suspensions, gels, emulsions, salves, pastes, or aerosols. They are preferably used in hair care preparations. In addition to the active substance combination according to the invention, these cosmetic preparations may contain standard auxiliaries and vehicles, such as water, organic solvents, surface-active compounds, oils, fats, waxes, fragrances, dyes, preservatives and the like. The new sebosuppressive preparations best contain from 0.01% to 10% by weight and preferably from 0.05% to 5% by weight of the p-alkoxy benzoic acid derivatives.

The preparations according to the invention can be used daily, but satisfactory results are already obtained with a single weekly application. The individual dose to be used in each treatment is not critical. Harmful side effects are not observed. The greasy appearance of the hair is reduced, and fat production delayed, so that normal hair care is possible.

If the preparation according to the invention is used in the form of hair creams or hair milk preparations or shaking mixtures, it is possible to improve the appearance permanently by regular application on the skin.

The following examples will illustrate the subject of the invention without limiting it, however, to these examples.

PRODUCTION EXAMPLES

(A) p-decyloxybenzoic acid 2-methoxy-ethyl ester

(a) p-hydroxybenzoic acid 2-methoxy-ethyl ester

A mixture of 25.0 g of p-hydroxybenzoic acid, 170 g of methyl glycol (methoxyethanol) and 1 ml of sulfuric acid (conc.) was heated for 8 hours to 110°–115° C. and, after the excess methyl glycol had been distilled off under reduced pressure, was poured onto ice/water. After neutralization with sodium hydrogen carbonate, the aqueous phase was extracted by shaking several times with methylene chloride. The methylene chloride solution was treated with active carbon, concentrated by evaporation and the residue recrystallized from toluene. p-hydroxybenzoic acid 2-methyloxy-ethyl ester melting at 90°–93° C. was obtained in a yield of 27.6 g (78%).

(b) p-decyloxybenzoic acid 2-methoxy-ethyl ester

A mixture of freshly prepared sodium ethanolate (from 2.3 g (0.1 mol) of sodium and 100 ml of ethanol, evaporated to dryness), 250 ml of dried dimethylformamide, 19.6 g (0.1 mol) of p-hydroxybenzoic acid 2-methyloxy-ethyl ester and 17.7 g (0.1 mol) of decyl chloride was heated for 4 hours to boiling temperature and subsequently concentrated under an oil pump vacuum. The residue was taken up in petroleum ether and washed 3 times with water. The petroleum ether solution was dried with $Na_2SO_4$ and concentrated by evaporation. 25.5 g of p-decyloxybenzoic acid 2-methoxy-ethyl ester still slightly contaminated with starting product were obtained in this way. Purer ester was obtained by column chromatography ($SiO_2$, Merck/methylene chloride+2% of methanol). Refractive index: $n_D^{20} = 1.4971$.

(B) p-decyloxybenzoic acid 2-ethoxy-ethyl ester

This ester was produced in the same way as in A, starting from ethyl glycol (ethoxyethanol). The ester had a refractive index: $n_D^{20} = 1.4932$.

(C) p-decyloxybenzoic acid 2-(2-methoxyethoxy)-ethyl ester

A mixture of 25 g (0.09 mol) of p-decyloxybenzoic acid methyl ester and 100 ml of diethylene glycol monomethyl ether was heated for 6 hours to 150° C. with a spatula tip of sodium methanolate. After the excess diethylene glycol monomethyl ether had been distilled off, the residue was taken up in methylene chloride, the solution was washed with water, treated with active carbon and concentrated by evaporation. 24.5 g (72%) of slightly contaminated p-decyloxybenzoic acid 2-(2-methoxyethoxy)-ethyl ester were obtained. Purification by column chromatography ($SiO_2$, Merck/methylene chloride+5% of methanol) produced pure ester having a refractive index $n_D^{20}$ of 1.4945.

(D) p-decyloxybenzoic acid 2-hydroxy-ethyl ester

This ester was produced in the same way as in C, starting from ethylene glycol. The ester had a melting point of 42°–44° C.

(E) p-decyloxybenzoic acid 2-diethylaminoethyl ester

This ester was produced in the same way as in C, starting from diethylaminoethanol. The ester had a refractive index: $n_D^{20} = 1.4975$.

(F) p-dodecyloxybenzoic acid 2-methoxy-ethyl ester

This ester was produced in the same way as in A, starting from dodecyl chloride. The ester had a refractive index: $n_D^{20} = 1.4945$.

(G) p-decyloxybenzoyloxy-acetic acid methyl ester

Following the addition of 11.2 g (73 mMols) of bromoacetic acid methyl ester, a suspension of 20 g (67 mMols) of p-decyloxybenzoic acid, sodium salt, in 100 ml of methanol was heated for 3 hours and, after the addition of another 2 ml of bromoacetic acid methyl ester, for another 1.5 hours to boiling temperature. After the volatile constituents had been distilled off, the residue was extracted cold with methylene chloride, the solution was washed with water, concentrated by evaporation, the oily residue was taken up in petroleum ether, the solution was treated with active carbon and then reconcentrated by evaporation. p-decyloxybenzoyloxy acetic acid methyl ester melting at 30° to 32° C. was obtained in a yield of 15.8 g (68%). Purification by column chromatography ($SiO_2$, Merck/methylene chloride:toluene=7:3) produced pure ester melting at 32.5° to 34° C.

The antiseborrheic effect was closely studied using the animal tests described in the following:

The test animals were male Wistar rats having a body weight of 220 to 230 g at the beginning of the tests. The degree of browning on the shaved back of the rats was visually assessed. Browning is produced by the brown skin surface lipid of the rats. This test is based on the observation that young female rats and also male rats washed with a tenside solution or with a lipid solvent and also male rats systematically treated with estrogen only have the normal light, pink-colored skin after shaving. At the same time, only comparatively very small quantities of lipids can be extracted from the shaved hair.

In order to assess effectiveness, the test substances in solution in alcohol were each brushed onto half the back of 6 rats. The other half was only treated with the solvent minus active substances.

Over the test period of 14 days, the test substances were applied once daily for a total of 9 days. A group of 6 rats which remained completely untreated was used for further control. At the end of the test, the animals were shaved on their back and sides and were visually assessed independently by an examination panel of 6 people under double blind conditions.

Evaluation methods:

The first criterion evaluated was whether the majority of examiners correctly recognized the treated side, differentiation being carried out as follows:

| Symbol | Percentage of examiners noticing an effect |
|---|---|
| ++ | 100% |
| + | >50%–100% |
| − | ≦50% |

The second criterion evaluated was the difference between the righthand side and the lefthand side, each examiner having to award 1 point per animal on the following basis:
 darker side—1 point
 lighter side—0 point and
 both sides the same—0.5 point Significant differences between the untreated and treated sides in the second method of evaluation indicate the local effectiveness of a substance.

The third criterion evaluated was the difference in intensity between the shades of brown using the following scale:

3 points dark brown,
2 points medium brown,
1 point light brown,
0 points no browning.

In the third method or evaluation, the points total differences are worked out between the untreated control animals and the treated and untreated sides of the test animals, significant differences between the control animals and the treated side of the test animals again indicating the effectiveness of a substance.

At the same time, there is generally also a distinct difference between the untreated and treated sides of the groups of test animals. However, this difference is not always as clear as that between the control animals and the treated sides, for which there may be various reasons, including for example mechanical transfer of substance from one side to the other or solvent influence.

The following scheme was used for differentiating the effects according to evaluation methods 2 and 3:

| Symbol | Points difference |
|---|---|
| ++ | very large ($\geq$99.9% probability) |
| + | significant ($\geq$95% probability) |
| − | (<95% probability) |

Percentage sebum reduction

The sebum reduction is calculated from the points difference by working out the quotient between the points difference $\Delta P$ and the number of points for the control group $P_k$ and expressing the value obtained in percent.

Sebum reduction = $(\Delta P/P_k) \cdot 100 [\%]$

The p-alkoxybenzoic acid esters were applied in the manner described in concentrations of 0.1%, 0.2% and 1.0% in alcohol. The results are set out in the following Table.

TABLE

| | | Evaluation of the sebosuppressive effects | | | |
|---|---|---|---|---|---|
| | | Evaluation method | | | Sebum reduction |
| Compound | Conc. (%) | 1 | 2 | 3 | (%) |
| A | 1.0 | ++ | ++ | ++ | 100 |
| | 0.1 | ++ | ++ | ++ | 69 |
| B | 1.0 | ++ | ++ | ++ | 93 |
| | 0.1 | ++ | ++ | ++ | 30 |
| C | 1.0 | ++ | ++ | ++ | 100 |
| | 0.1 | ++ | ++ | ++ | 26 |
| D | 1.0 | ++ | ++ | ++ | 98 |
| E | 1.0 | ++ | ++ | ++ | 90 |
| | 0.1 | ++ | ++ | ++ | 80 |
| F | 1.0 | ++ | ++ | ++ | 91 |
| | 0.2 | ++ | ++ | ++ | 92 |
| G | 0.5 | ++ | ++ | ++ | 82 |

Examples of formulations

Formulations for the topical preparations according to the invention for the treatment of very greasy hair and seborrheic skin are given in the following:

| | Parts by weight |
|---|---|
| 1. Shampoo for greasy hair | |
| Ammonium lauryl sulfate containing 33 to 35% of washing-active substance (Texapon A ®) | 40.0 |
| Coconut oil fatty acid diethanolamide (Comperlan KD ®) | 3.0 |
| Sodium chloride | 2.0 |
| Sodium sulfate | 2.0 |
| Compound of Example A | 1.0 |
| Preservative | 0.1 |
| Perfume oil | 0.1 |
| Water | ad 100 |
| 2. Hair treatment composition | |
| Glycerol mono-distearate (Tegin M ®) | 0.7 |
| Cationic tenside | 2.0 |
| Cholesterol | 0.2 |
| Soy lecithin | 0.3 |
| Emulgade A ® (a mixture of cetyl/stearyl alcohol with nonionic emulsifiers) | 8.0 |
| Perfume oil | 0.3 |
| Compound of Example D | 1.0 |
| Water, fully deionized | ad 100 |
| 3. Skin cream | |
| Self-emulsifying mixture of mono/diglycerides of higher saturated fatty acids with potassium stearate (Cutina KD 16 ®) | 16.0 |
| Cetyl/stearyl alcohol containing approximately 12 mols of ethylene oxide (Eumulgin B1 ®) | 1.0 |
| 2-octyldodecanol | 6.0 |
| Isopropyl myristate | 4.0 |
| Glycerol | 6.0 |
| Compound of Example F | 2.0 |
| Water | ad 100 |

Suppliers of the commercial products mentioned:
Texapon A ® = Henkel KGaA
Comperlan KD ® = Henkel KGaA
Emulgrade A ® = Henkel KGaA
Cutina KD 16 ® = Henkel KGaA
Eumulgin B 1 ® = Henkel KGaA
Tegin M ® = Atlas-Chemie The preceding specific embodiments are illustrative of the practice of the invention. It is to be understood, however, that other expedients known to those skilled in the art or described herein, may be employed without departing from the spirit of the invention or the scope of the appended claims.

We claim:

1. A topical cosmetic preparation for the treatment of seborrhea containing a sebosuppressively effective amount of at least one alkoxybenzoic acid ester having the formula

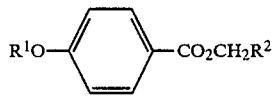

wherein $R^1$ represents a $C_{6-20}$-n-alkyl and $R^2$ is a member selected from the group consisting of —$CH_2OR^3$, —$C_2H_4OR^3$, —$CH_2OC_2H_4OR^3$, —$CH_2OH$, —$C_2H_4OH$, —$CH(CH_3)OH$, —$CH_2NR^3R^4$, —$C_2H_4NR^3R^4$, —$CO_2R^3$ and —$CH_2CO_2R^3$, wherein $R^3$ and $R^4$ are $C_{1-4}$-alkyl, as an antiseborrheic, and further containing conventional vehicles and additives for topical application.

2. The topical cosmetic preparation of claim 1 wherein said at least one alkoxybenzoic acid ester is present in an amount of from 0.01% to 10.0% by weight.

3. The topical cosmetic preparation of claim 1 wherein said at least one alkoxybenzoic acid ester is present in an amount of from 0.05% to 5.0% by weight.

4. A process for reducing sebaceous cell sebum production in a mammal in need thereof which comprises contacting said sebaceous cell in the skin of said mammal with an effective amount to reduce sebum production of at least one alkoxybenzoic acid ester having the formula

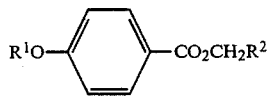

wherein $R^1$ represents a $C_{6-20}$-n-alkyl and $R^2$ is a member selected from the group consisting of $-CH_2OR^3$, $-C_2H_4OR^3$, $-CH_2OC_2H_4OR^3$, $-CH_2OH$, $-C_2H_4OH$, $-CH(CH_3)OH$, $-CH_2NR^3R^4$, $-C_2H_4NR^3R^4$, $-CO_2R^3$ and $-CH_2CO_2R^3$, wherein $R^3$ and $R^4$ are $C_{1-4}$-alkyl.

5. An alkoxybenzoic acid ester having the formula

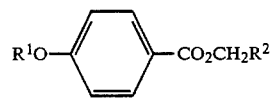

wherein $R^1$ represents a $C_{6-20}$-n-alkyl and $R^2$ is a member selected from the group consisting of $-CH_2OR^3$, $-C_2H_4OR^3$, $-CH_2OC_2H_4OR^3$, $-CH_2OH$, $-C_2H_4OH$, $-CH(CH_3)OH$, $-CH_2NR^3R^4$, $-C_2H_4NR^3R^4$, $-CO_2R^3$ and $-CH_2CO_2R^3$, wherein $R^3$ and $R^4$ are $C_{1-4}$-alkyl.

6. The alkoxybenzoic acid ester of claim 5 wherein $R^1$ is n-decyl and $R^2$ is $-CH_2OCH_3$.

7. The alkoxybenzoic acid ester of claim 5 wherein $R^1$ is n-decyl and $R^2$ is $-CH_2OC_2H_5$.

8. The alkoxybenzoic acid ester of claim 5 wherein $R^1$ is n-decyl and $R^2$ is $-CH_2OC_2H_4OCH_3$.

9. The alkoxybenzoic acid ester of claim 5 wherein $R^1$ is n-decyl and $R^2$ is $-CH_2OH$.

10. The alkoxybenzoic acid ester of claim 5 wherein $R^1$ is n-decyl and $R^2$ is $-CH_2N(C_2H_5)_2$.

11. The alkoxybenzoic acid ester of claim 5 wherein $R^1$ is n-dodecyl and $R^2$ is $-CH_2OCH_3$.

12. The alkoxybenzoic acid ester of claim 5 wherein $R^1$ is n-decyl and $R^2$ is $-CO_2CH_3$.

* * * * *